US005127235A

United States Patent [19]

Nakanishi et al.

[11] Patent Number: 5,127,235

[45] Date of Patent: Jul. 7, 1992

[54] LOW NOISE REFRIGERATOR AND NOISE CONTROL METHOD THEREOF

[75] Inventors: Keiji Nakanishi; Yasuyuki Sekiguchi, both of Osaka, Japan

[73] Assignee: Kabushiki Kaisha Toshiba, Kawasaki, Japan

[21] Appl. No.: 626,042

[22] Filed: Dec. 14, 1990

[30] Foreign Application Priority Data

Dec. 18, 1989 [JP] Japan ........ 1-327786
Dec. 18, 1989 [JP] Japan ........ 1-327788

[51] Int. Cl.[5] ........ A61F 11/06; H03B 29/00

[52] U.S. Cl. ........ 62/115; 62/296; 181/206; 381/71

[58] Field of Search ........ 381/71, 73.1, 94; 62/296, 115; 417/14, 312; 181/202, 200, 206

[56] References Cited

U.S. PATENT DOCUMENTS 2,043,416 6/1936 Lueg ........ 179/1
4,025,724 5/1977 Davidson, Jr. et al. ........ 181/206 X
4,044,203 8/1977 Swinbanks ........ 181/206 X
4,153,815 5/1979 Chaplin et al. ........ 179/1

FOREIGN PATENT DOCUMENTS 63-311397 12/1988 Japan .

OTHER PUBLICATIONS

IBM Technical Disclosure Bulletin, vol. 31, No. 8, pp. 256–258 "Audible Noise Suppression".

*Primary Examiner*—William E. Wayner
*Attorney, Agent, or Firm*—Foley & Lardner

[57] ABSTRACT

In a low noise refrigerator, a rotary compressor constituting a noise source is arranged within a machine chamber provided with an opening in one location, which chamber has a one-dimensional duct construction having a cross-sectional dimension which is small relative to trhe wavelength of the noise which is to be reduced. A vibration pick-up being located in the vicinity of the rotary compressor. The vibration pick-up detects compressor vibrations which correlate to the compressor noise, in the tangential direction of the compressor. There is provided a control circuit that processes the output signal of the vibration pick-up. In the machine chamber, a sound generator is driven by the output signal of the control circuit to generate a control sound, so that the compressor noise which tries to issue from the opening is canceled by the control sound.

14 Claims, 8 Drawing Sheets

LOW NOISE REFRIGERATOR AND NOISE CONTROL METHOD THEREOF

BACKGROUND OF THE INVENTION

1. Field of the Invention

The present invention relates, in general to a low noise refrigerator equipped with a silencing system adopting a so-called active control method.

2. Description of the Related Art

Recently, attempts have been made to lower the noise produced by the compressor and fan motor of a refrigerator, which constitute the principal sources of refrigeration noise. Progress has been made with anti-vibration designs for the refrigerant piping within the machinery chamber that accommodates the compressor. Also, by use of sound absorbing and sound insulating materials or mufflers, reduction of the high frequency components of compressor noise has been achieved to some degree. However, there is a problem that sufficient noise reduction can not be achieved by these conventional techniques in the low frequency noise band in particular.

Therefore, the inventors of the present invention have studied the application of a silencing system adopting a so-called active control method to refrigerators. In an active controlled silencing system, noise is canceled by actively emitting a controlled sound from, for example, a speaker. The noise source is detected by using a microphone such as described in U.S. Pat. No. 2,043,416. Japanese Patent Disclosure (Kokai) No. 63-311397 discloses that at least a section of the sound wave propagation path, where the silencing system is located, is constructed of a special material such as a vibration stopper or vibration absorbent. One example of the application of an active control silencing system to a refrigerator is shown in FIG. 12. The contents of FIG. 12 are presented for explanation, not as a description of the prior art. In FIG. 12, a compressor 120 is arranged in a machine chamber 110 that is located at the lowest part at the back face of the refrigerator. The compressor 120 is the main source of refrigerator noise. The machine chamber 110 has a one-dimensional duct construction, being completely sealed except for a single opening 117 for heat radiation and evaporation of defrosting water. That is, by making the dimensions of the cross-section of the duct sufficiently small in comparison with the wavelength of the compressor noise S that is to be reduced, the compressor noise S in the machine chamber 110 can be made to be a one-dimensional plane-progressive wave. The compressor noise S is detected by a microphone 135 that is arranged in a position within the machine chamber 110 remote from the opening 117. The compressor noise i.e., the sound M that is detected by the microphone 135 is processed by a control circuit 140 of transfer function G. Circuit 40 is equipped with a finite impulse response filter (hereafter, FIR filter) that for example, directly processes the digital signal in the time domain, before supplying a compressor noise signal to the speaker 150. The compressor noise that tries to get out from the opening 117 of the machine chamber 110 is canceled by the controlled sound A produced by the speaker 150.

The transfer function G of the control circuit 140 is determined as follows. The detected sound M obtained by the microphone 135 can be represented by equation (1) below, in terms of the noise S emitted from the compressor 120 and the controlled sound A emitted from the silencing speaker 150, using the sound transfer function $G_{SM}$ between the compressor and the microphone and the sound transfer function $G_{AM}$ between the speaker and the microphone.

$$M = S \times G_{SM} + A \times G_{AM} \quad (1)$$

For test purposes, a microphone 155 for evaluation of the silencing effect is provided at the opening 117 of the machine chamber 110. The measured sound R of the evaluation microphone 155 can be expressed by equation (2) below, using the sound transfer function $G_{SR}$ between the compressor and the opening, and the sound transfer function $G_{AR}$ between the speaker and the opening.

$$R = S \times G_{SR} + A \times G_{AR} \quad (2)$$

Since G is the transfer function between the microphone and the speaker, the following equation (3) holds.

$$A = M \times G \quad (3)$$

In order to cancel the compressor noise that tries to issue from the opening 117, the following equation (4) should be held.

$$G = 0 \quad (4)$$

From above equations (1) to (4), the transfer function G for silencing is expressed by the following equation (5).

$$G = G_{SR}/(G_{SR} \times G_{AM} = G_{SM} \times G_{AR}) \quad (5)$$

If the numerator and the denominator of the equation (5) is divided by $G_{SM}$, the following equation (6) is obtained. $G_{MR}$ is defined by equation (7).

$$G = G_{MR}/(G_{MR} \times G_{AM} - G_{AR}) \quad (6)$$

$$G_{MR} = G_{SR}/G_{SM} \quad (7)$$

By using these equations (6) and (7), even if the compressor noise S is unknown, the transfer function G to make the measured sound R zero can be found by measuring the transfer function ratio $G_{MR}$ between $G_{SR}$ and $G_{SM}$. On this occasion, in the condition in which noise S is generated from the compressor 120, the detected sound may be treated as an input signal and the measured sound R may be treated as a response signal.

If a transfer function G determined as above is supplied to control circuit 140, a controlled sound A corresponding to compressor noise S is generated and the noise S is canceled at the opening 117 of the machine chamber 110.

However, when the compressor noise S is detected by the microphone 135, the following problems occur. First of all, since not only the noise S from the compressor 120 but also the controlled sound A from silencing speaker 150 is picked up by the microphone 135, howling can occur. Therefore, the output of the speaker 150 must be kept fairly low, resulting in an inadequate silencing effect. An echo canceler can be fitted into control circuit 140 to prevent howling, but this raises the cost of the system. Also, if a fan for cooling the compressor 120 is provided in machine chamber 110, the noise generated by the fan will also be picked-up by the microphone 135, making the control for silencing more complicated. Furthermore, there is a risk that the silencing system would react to, for example, an external noise.

SUMMARY OF THE INVENTION

Accordingly, it is an object of the present invention to provide a refrigerator with an active control silencing system wherein howling is avoided.

It is further object of the present invention to provide a refrigerator having an active control silencing system which is not affected by sounds other than compressor noise.

In accordance with the present invention, the foregoing objects are achieved by providing a refrigerator with a silencer system.

The refrigerator includes a rotary compressor, a machine chamber, a vibration pick-up, a control circuit and a sound generator. The rotary compressor compresses a refrigerant and constitutes a substantial noise source. The machine chamber accommodates the rotary compressor. The machine chamber is provided with an opening in one location. The chamber has a one-dimensional duct construction in which the cross-sectional dimension of the duct is small relative to the wavelength of the compressor noise to be reduced. The vibration pick-up detects compressor vibrations in the tangential direction of the rotary compressor, which correlate to the compressor noise. The vibration pick-up is located in the vicinity of the rotary compressor. The control circuit processes an output signal of the vibration pick-up. The sound generator generates a control sound corresponding to the compressor noise. The sound generator is driven by an output signal from the control circuit.

BRIEF DESCRIPTION OF THE DRAWINGS

These and other objects and advantages of this invention will become more apparent from the following detailed description of the presently preferred embodiment of the invention, taken in conjunction with the accompanying drawings of which.

DETAILED DESCRIPTION OF THE PREFERRED EMBODIMENTS

Figure 1:
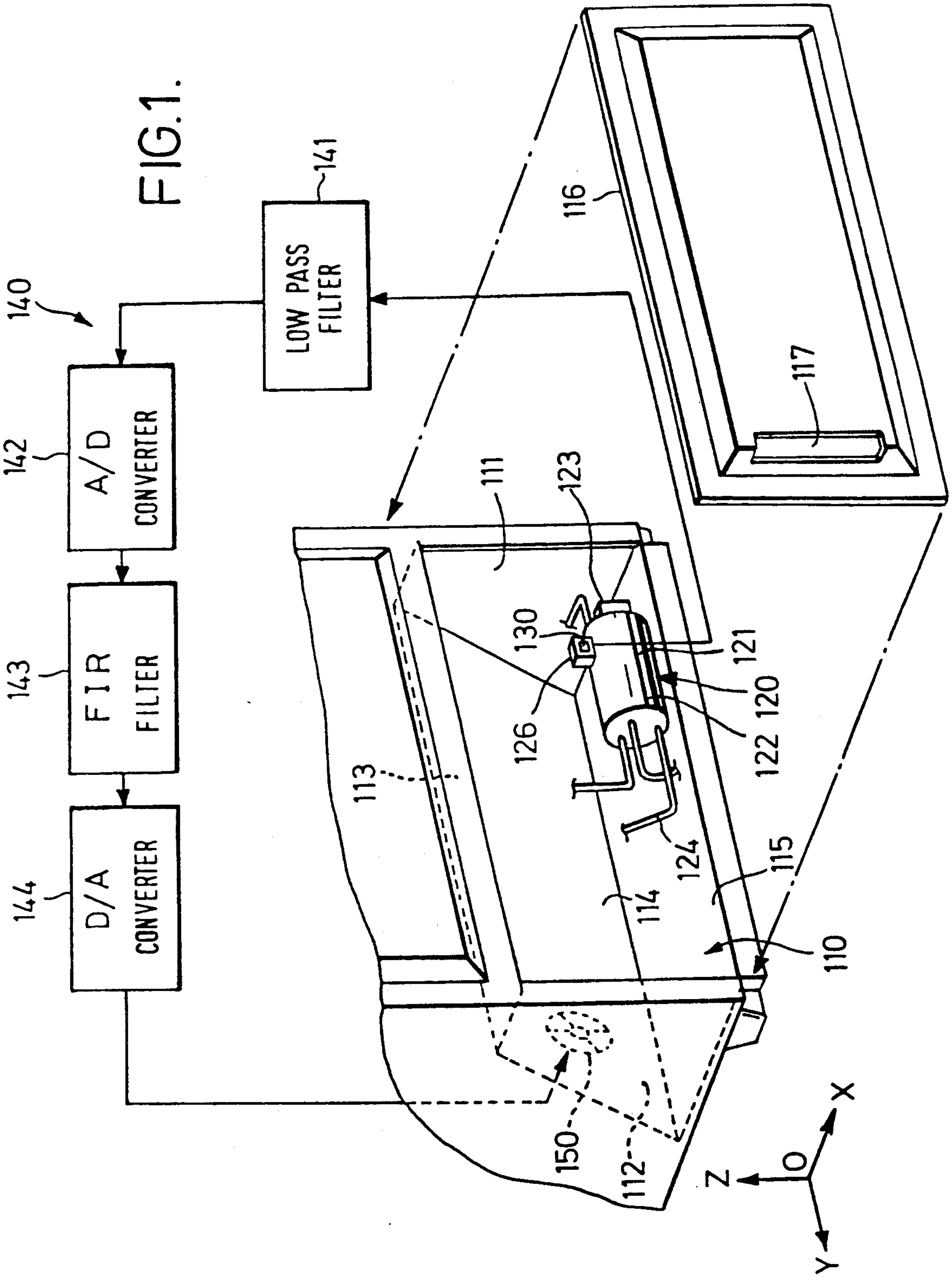
FIG. 1 is an exploded perspective view of the lowest part at the back face of a low noise refrigerator according to a first embodiment of the present invention.

The preferred embodiment of the present invention will now be described in more detail with reference to the accompanying drawings. Like reference numerals designate like or corresponding parts throughout the drawings.

In FIG. 1, a rotary compressor 120 is arranged in machine chamber 110 which is positioned at the lowest part of the back face of the refrigerator. The rotary compressor 120 is the main noise source. The machine chamber 110 is closed by means of two side plates 111, 112, a ceiling plate 113, a front inclined plate 114, a bottom plate 115 and a back face cover 116. Thus, the machine chamber !10 is completely closed with the exception of a single opening 117 for heat radiation etc. that is provided at the left end of the cover 116 seen from the back face of the refrigerator. Taking the X axis in the forwards/rearwards direction of the refrigerator, the Y axis in the left/right direction and the Z axis in the vertical direction, the machine chamber 110 has a one-dimensional duct construction in the direction of the Y axis. That is, the cross-sectional dimension in the X-Z plane of the machine chamber 110 is small relative to the wavelength of the compressor noise that is to be reduced. Therefore, the compressor noise becomes a one-dimensional plane-progressive wave in the direction of the Y axis. Specifically, by taking the dimension in the direction of the Y axis (duct length) of the machine chamber 110 as for example 640 mm or 880 mm, and taking the dimensions in the X axis and Z axis directions as about 250 mm, the machine chamber 110 can be considered as a one-dimensional duct in the Y axis direction. Inasmuch as only the Y axis direction sound mode is generated at frequencies of less than 800 Hz. Emission of high frequency noise of over 800 Hz is prevented by mounting sound absorbent material consisting of elastic tape on the inner wall surface of the machine chamber 110. Therefore, the frequencies to be silenced by the active control silencing system of this embodiment are between 100 Hz and 800 Hz.

The major part of the noises which are generated by a rotary compressor are the rotation noise and the motor noise (electromagnetic noise). The rotation noise is generated by the rotation of the incorporated rotor. The rotation of the rotor creates vibrations in the direction tangential to the compressor body. These vibrations are radiated outside the body as rotational noise. On the otherhand, the motor noise is generated from a motor unit of the compressor 120.

The rotary compressor 120 is fixed in the Y axis direction at the right hand end position on the bottom plate 115 as shown in FIG. 1. The rotary compressor 120 has a cylindrical body. The right side of the body of the compressor 120 is a motor unit 121, while the left side of the body is the mechanical unit 122. A cluster unit 123 is provided at the end face on the side of the motor unit 121. A suction pipe 124 is connected to the end face on the side of the mechanical unit 122. A plate-shaped jig 126 that extends in the direction of the generating line i.e., the direction of the Y axis is erected on the circumferential surface of the body of the rotary compressor 120. A vibration pick-up 130 is mounted on the surface of the jig 126 with its normal in the direction of the X axis.

The tangential vibration of the compressor body is detected by the pick-up 130. The output signal of the vibration pick-up 130 is sent to a control circuit 140. The control circuit 140 is a cascade circuit consisting of a low pass filter 141, an A/D converter 142, an FIR filter 143 and a D/A converter 144. The output signal of the vibration pick-up 130 is processed by the control circuit 140 and is supplied to a speaker 150. The speaker 150 faces the opening 117 and is mounted at the left end of the front inclined plate 114 as shown in FIG. 1. The low pass filter 141 cuts off signals of frequency higher than one half of the sampling frequency of the A/D converter 142, in order to prevent the occurrence of aliasing error. The A/D converter 142 converts the analog signal that arrives through the low pass filter 141 into a digital signal that can be processed by the FIR filter 143. The FIR filter 143 carries out a convolution on the digital input signal, to create the prescribed output signal (convoluted integration value). The D/A converter 144 converts the digital signal that is output from the filter 143 to an analog signal, which it then supplies to the speaker 150. If the upper limit of the frequencies to be silenced is 800 Hz as described above, the sampling frequency should be as high as possible and at least 1.4 KHz. When the duct length is 640 mm, a sampling frequency of 6.4 KHz is suitable. When the duct length is 880 mm, a sampling frequency of 12.8 KHz is suitable.

Figure 2:
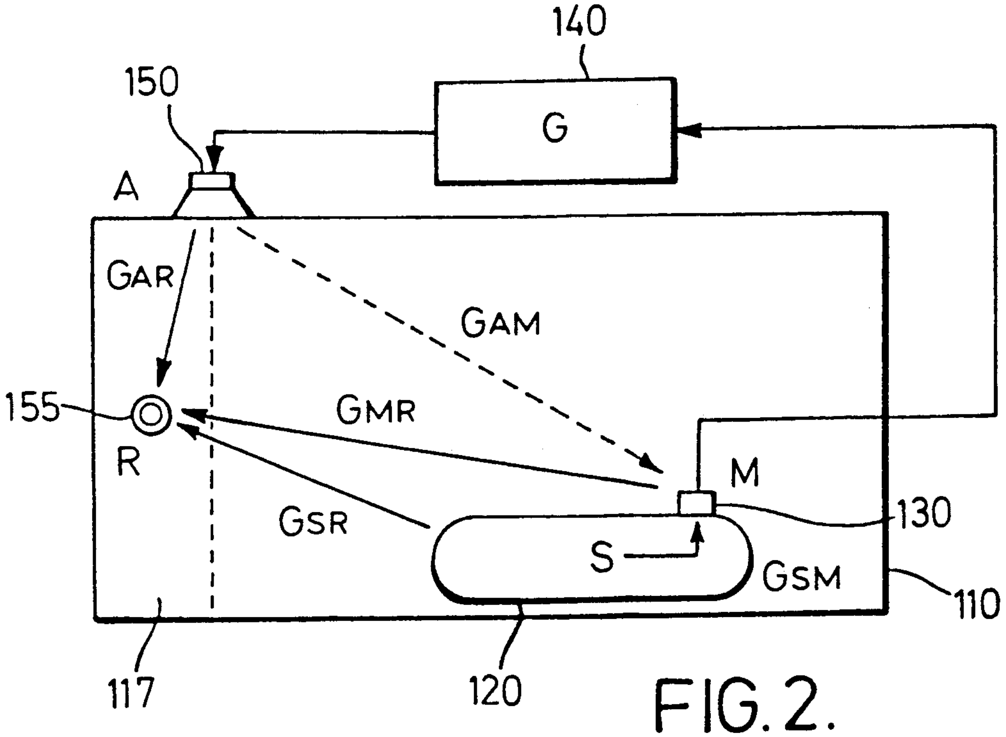
FIG. 2 is a diagram of an active control silencing system in FIG. 1.

FIG. 2 shows an active control silencing system of a low noise refrigerator according to the embodiment of this invention described above.

Figure 3:
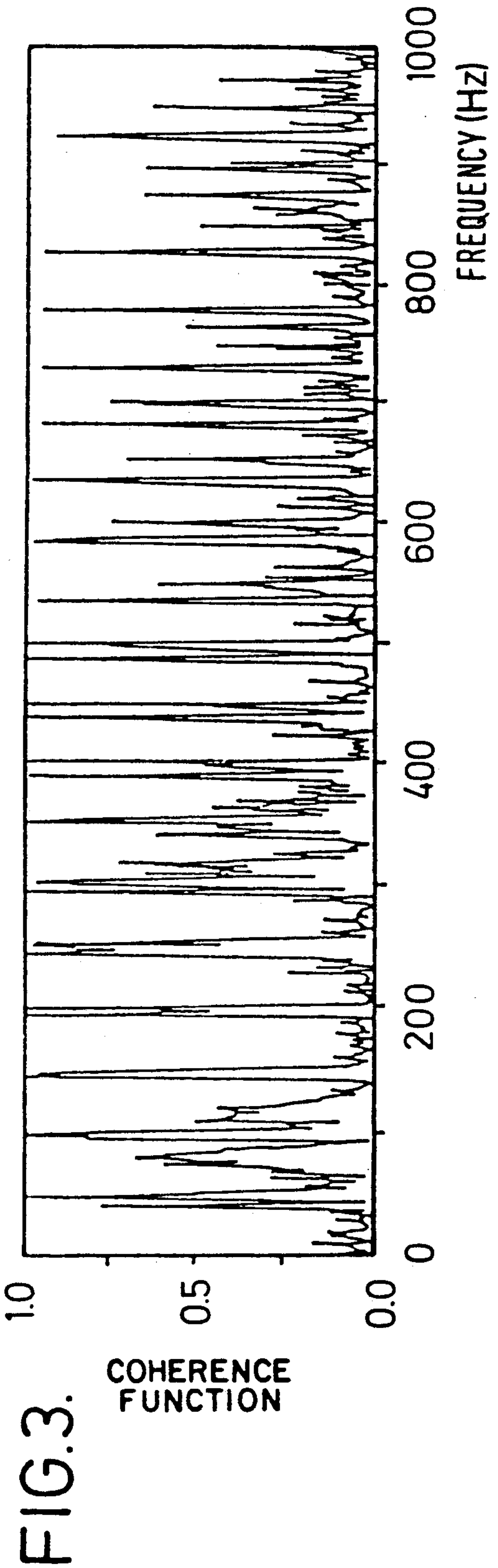
FIG. 3 is a graph showing the coherence function between vibration in the tangential direction of the compressor body measured at the vibration pick-up mounting position of FIG. 1 and compressor noise.
Figure 12:
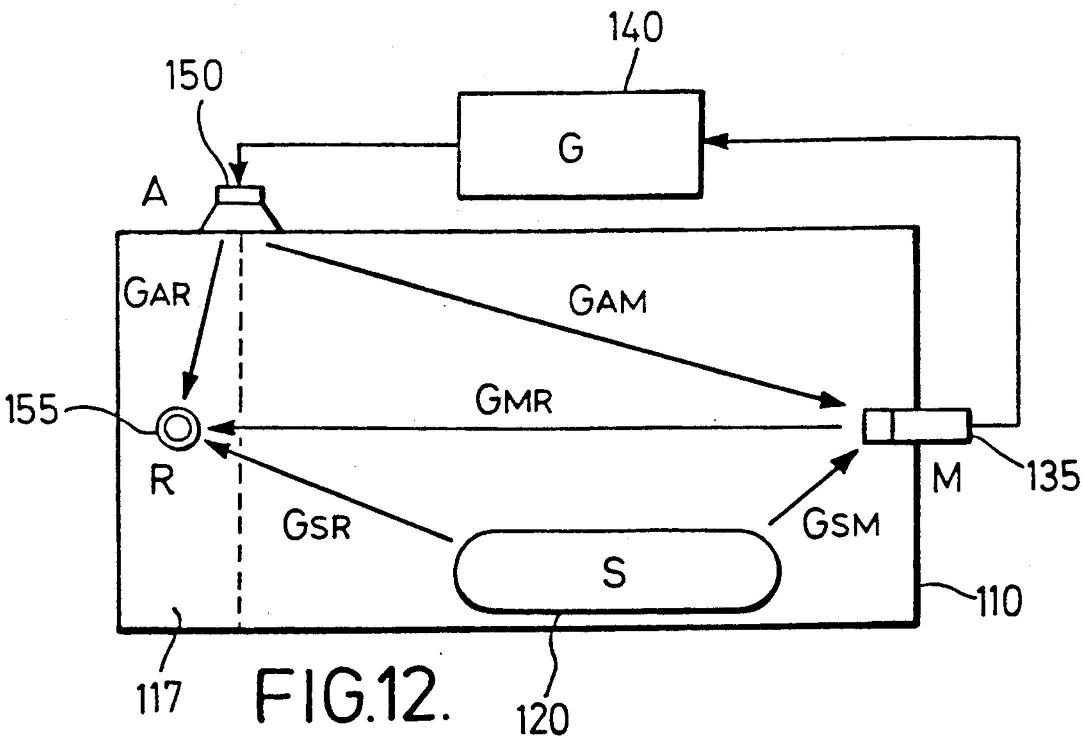
FIG. 12 is a diagram showing a comparative example of an active control silencing system for a low noise refrigerator.

In FIG. 2, the vibration pick-up 130 is employed instead of the microphone 135 shown in FIG. 12. FIG. 3 shows the coherence function between the vibration in the tangential direction of the body of the rotary compressor 120 detected by the pick-up 130 and the compressor noise detected by the microphone FIG. 3 shows the results of measurement of the coherence function using a two channel FFT (Fast Fourier Transform) analyzer. As is shown by FIG. 3, there is good correlation between the vibration in the tangential direction of the compressor body and the compressor noise S. That is, in constructing a silencing system, measurement of vibration in the tangential direction of the compressor body can be employed instead of detection of the compressor noise S. Furthermore, when a vibration pick-up 130 is employed, the sound transfer function $G_{AM}$ between speaker and pick-up becomes 0, as shown in FIG. 2 (following equation (8)).

$$G_{AM}=0 \tag{8}$$

If the equation (8) is substituted in equation (6) given above, the following equation (9), which is of very simple form, is obtained. $G_{MR}$ is the transfer function ratio of $G_{SR}$ and $G_{SM}$, and is defined by equation (7) given above.

$$G=-G_{MR}/G_{AR} \tag{9}$$

Figure 4:
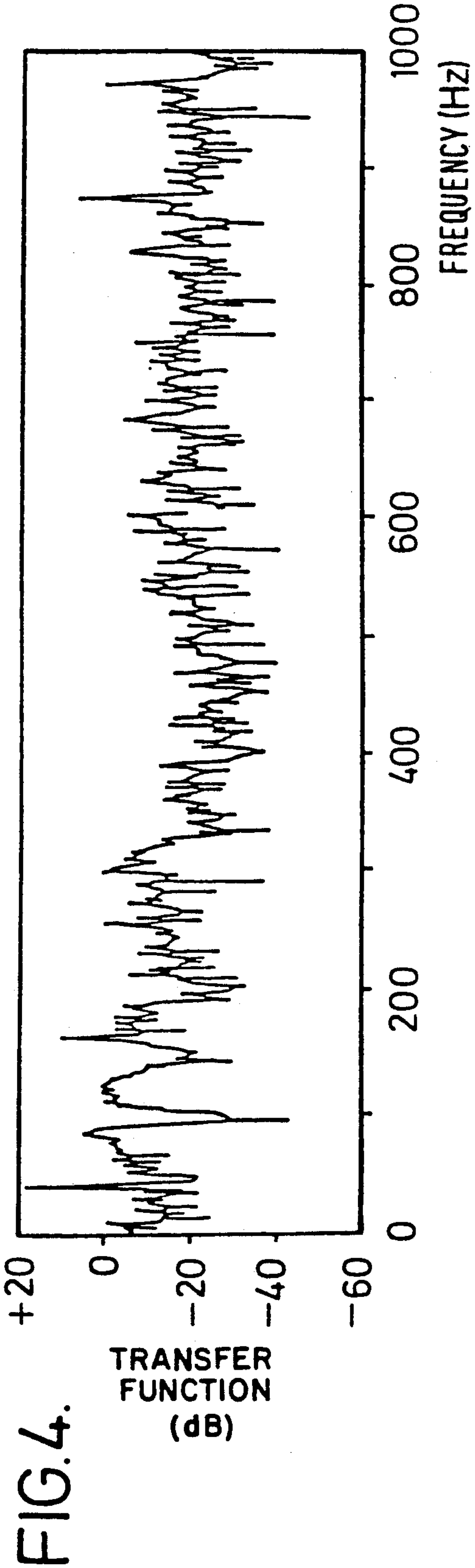
FIG. 4 is a view showing an example of the silencing transfer function G that is supplied to the control circuit of FIG. 1 and FIG. 2.

By using these equations (9) and (7), even if the compressor noise S is unknown, the transfer function G of the control circuit 140 in order to make the measured sound R zero at the opening 117 can be found by measuring the transfer function ratio $G_{MR}$. However, the noise that is emitted from the rotary compressor 120 has a discrete spectrum consisting of rotary noise and electromagnetic noise. Therefore, the transfer functions of the speed of revolution of the rotary compressor 120 and harmonics of the speed of revolution and the power source frequency and harmonics of the frequency should be treated as the only effective data. Furthermore, linear interpolation can be effected therebetween. FIG. 4 shows an example of a silencing transfer function G obtained as above. When the transfer function G is applied to the control circuit 140, the compressor noise S can be canceled at the machine chamber opening 117 by emitting from the speaker 150 a controlled sound A corresponding to the compressor noise S.

Figure 5:
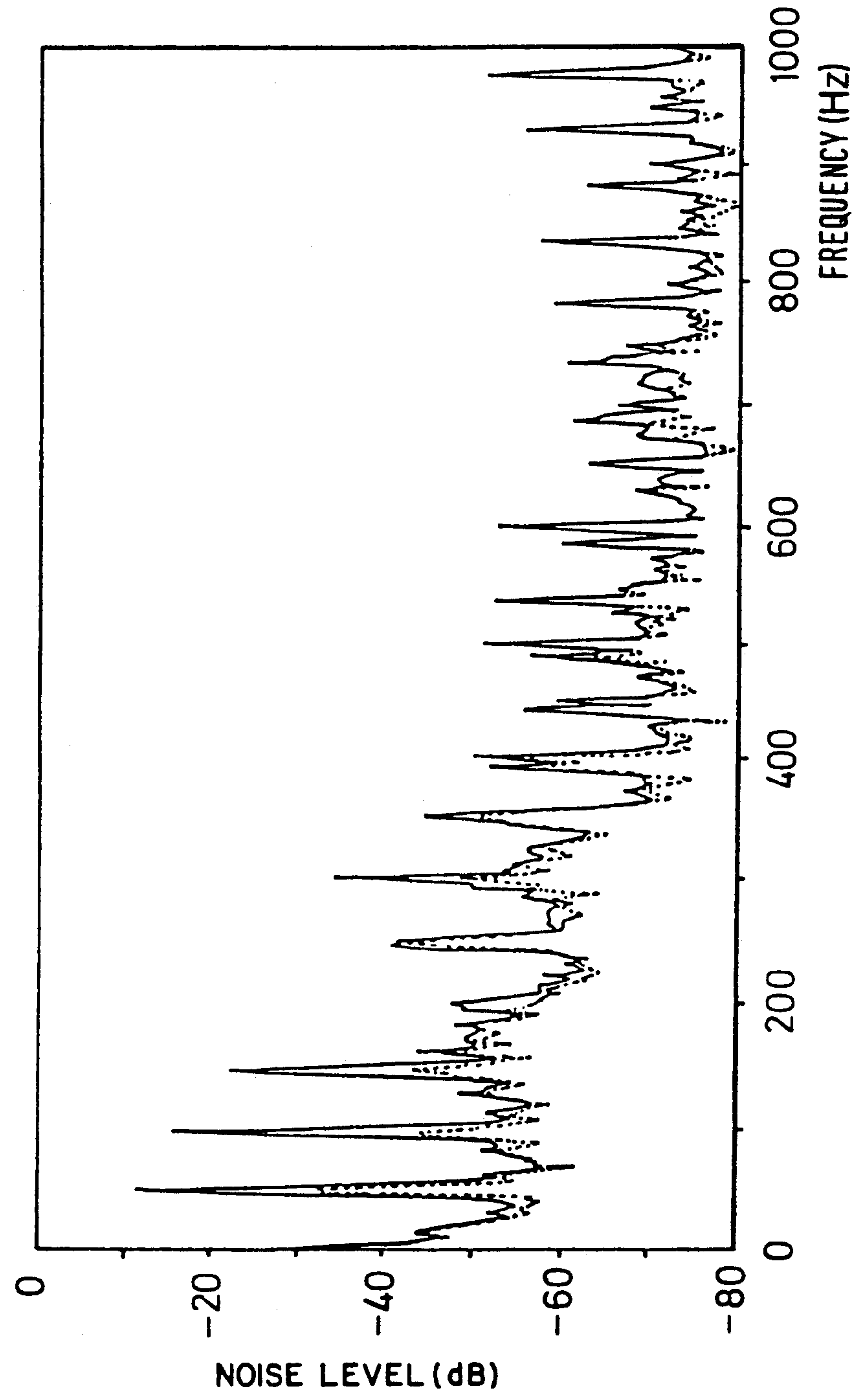
FIG. 5 is a noise level plot showing the noise reduction effect of the low noise refrigerator of FIG. 1.

FIG. 5 shows the noise reduction effect of such an active control silencing system. In FIG. 5, the continuous line indicates the noise level before silencing and the broken line indicates the noise level after silencing. With the embodiment shown in FIG. 5, a noise reducing effect of for example, 5 dB or more is obtained. The vibration pick-up 130 detects vibration in the tangential direction of the compressor body rather than the normal direction. Thus, the rotational noise of the rotary compressor can be detected with high sensitivity. Furthermore, since the compressor noise S is indirectly measured by the vibration pick-up 130, even if the output of the silencing speaker 150 is raised, there is no risk of the controlled sound A causing howling. In addition, there is no effect from noise other than the compressor noise S, such as fan noise or other external noise. However, the series of operations from pick-up of compressor vibration by the pick-up 130, processing of the compressor vibration to a silencing signal by the control circuit 140, input of the processed signal to the speaker 150, and the arrival of the controlled sound A from the speaker 150 at opening 117 must be completed before the sound emitted by the rotary compressor 120 reaches the opening 117. In order to make the processing time of the control circuit 140 as long as possible, the rotary compressor 120 is therefore placed as far as possible from the opening 117. Furthermore, the silencing speaker 150 is arranged as close as possible to the opening 117.

Figure 6:
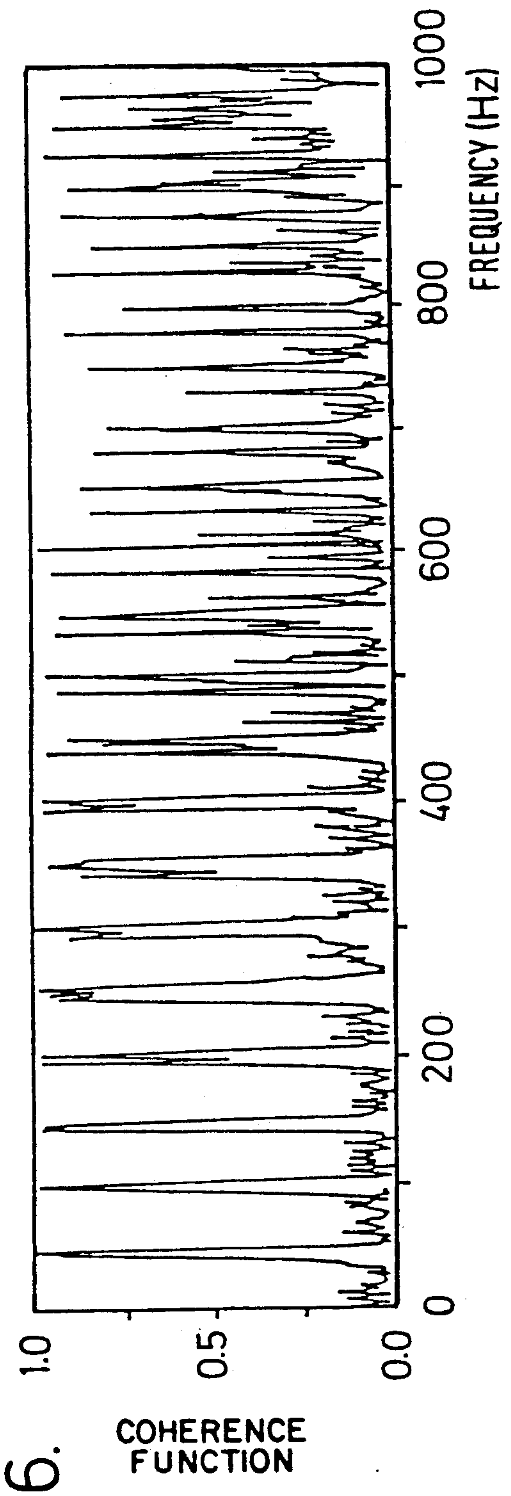
FIG. 6 is a graph showing the coherence function between vibration in the normal direction of the compressor body and compressor noise.
Figure 7:
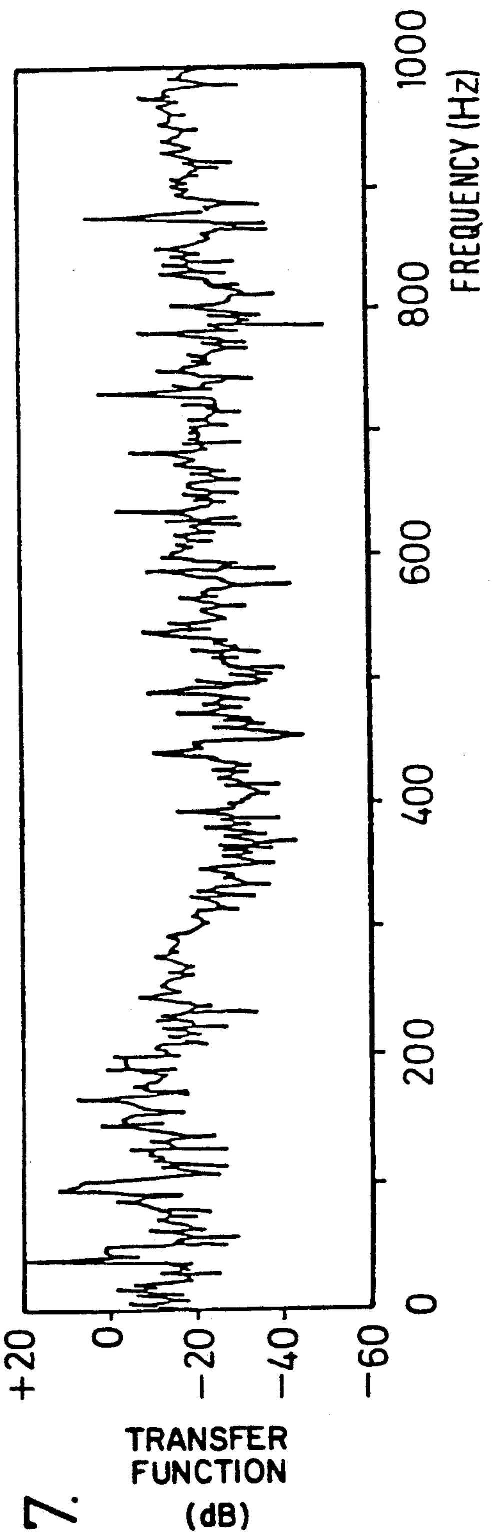
FIG. 7 is a graph showing an example of the silencing transfer function G that is supplied to the control circuit in the case of FIG. 6.
Figure 8:
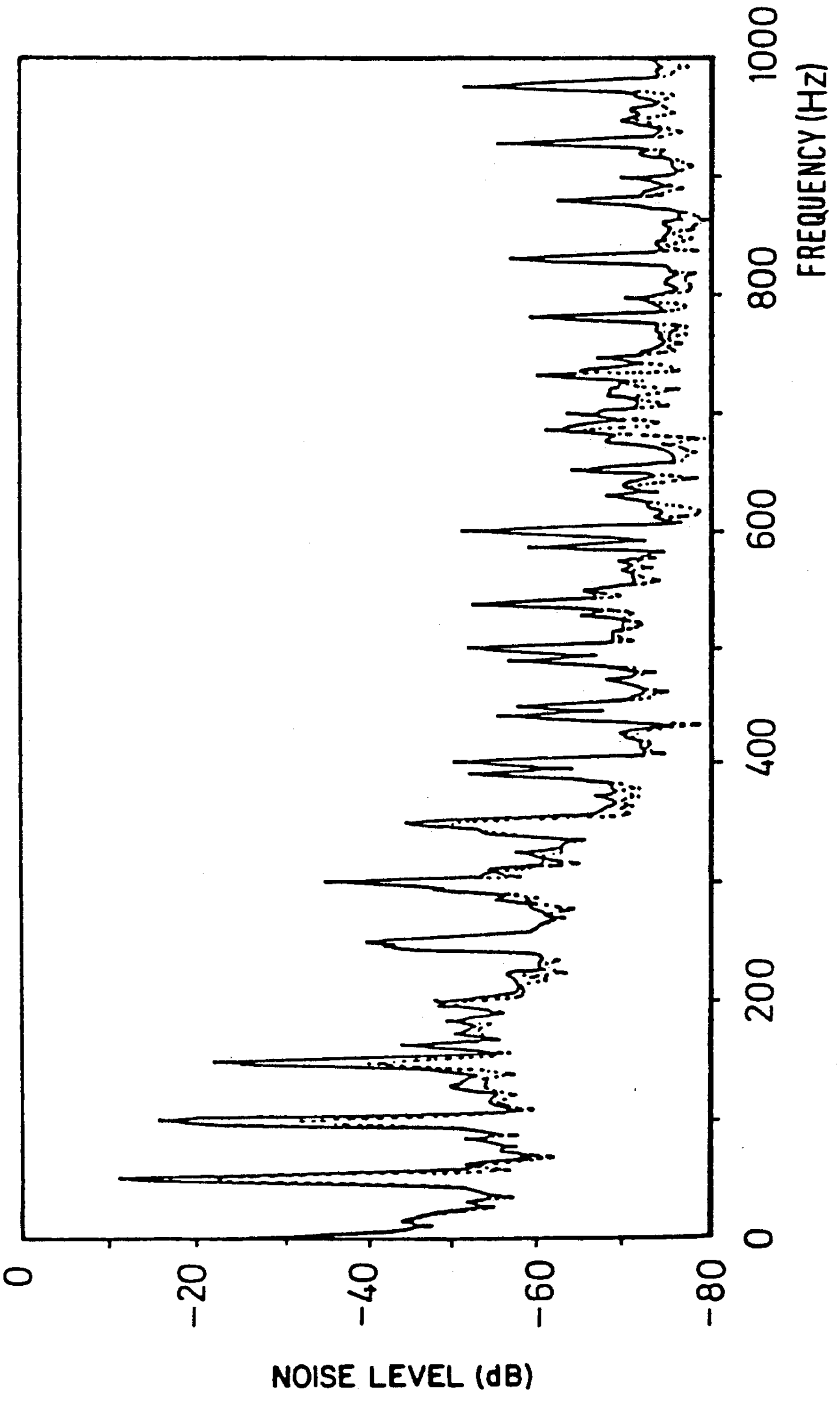
FIG. 8 is a noise level plot showing the noise reduction effect of a refrigerator when the silencing transfer function G of FIG. 7 is applied to the control circuit.

For comparison with the embodiment as shown in FIG. 1, FIG. 6 to FIG. 8, respectively corresponding to FIG. 3 to FIG. 5 described above, show the case where vibration is detected by the vibration pick-up in the normal direction of the compressor body. In this case, the sensitivity of vibration detection is decreased as shown in FIGS. 6 to 8.

Next, the vibration pick-up 130 may be mounted at the position where the vibration in the tangential direction of the compressor could be detected and is the neighborhood of the motor unit. In this case, the both of the rotationary noise and the motor noise are detected by the single vibration pick-up.

Figure 9:
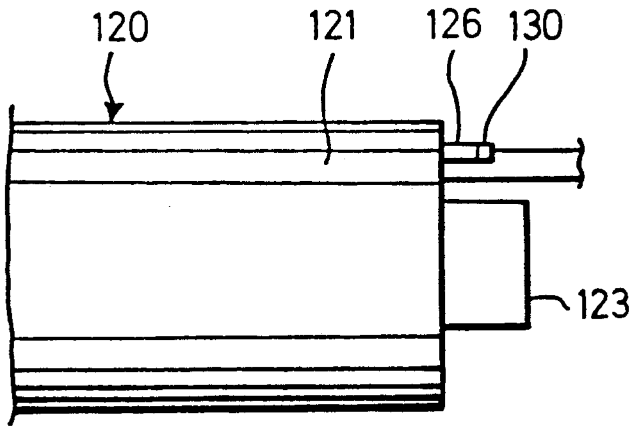
FIG. 9 is a side view of a compressor showing a vibration pick-up mounting position in a low noise refrigerator according to a second embodiment of the present invention.

FIG. 9 shows the mounting position of the vibration pick-up 130 in a low-noise refrigerator according to a second embodiment of the present invention. In the compressor 120, the end face of the motor unit 121, i.e., the end face of the cluster unit 123 of the main body, is close to the motor which is incorporated in the compressor 120 and in addition is flat. Thus, it is convenient for mounting of the vibration pick-up 130. In this embodiment, a bolt 126 is erected by welding on the end face of the motor unit 121. The vibration pick-up 130 is mounted on the bolt 126. Thus, the mounting of the vibration pick-up 130 is simple and secure, preventing failure in mounting. Even if a flat-sheet type vibration pick-up is directly mounted on the end face of the motor unit 121 without using the bolt 126, face contact between the compressor 120 and the vibration pick-up 130 can be achieved.

Figure 10:
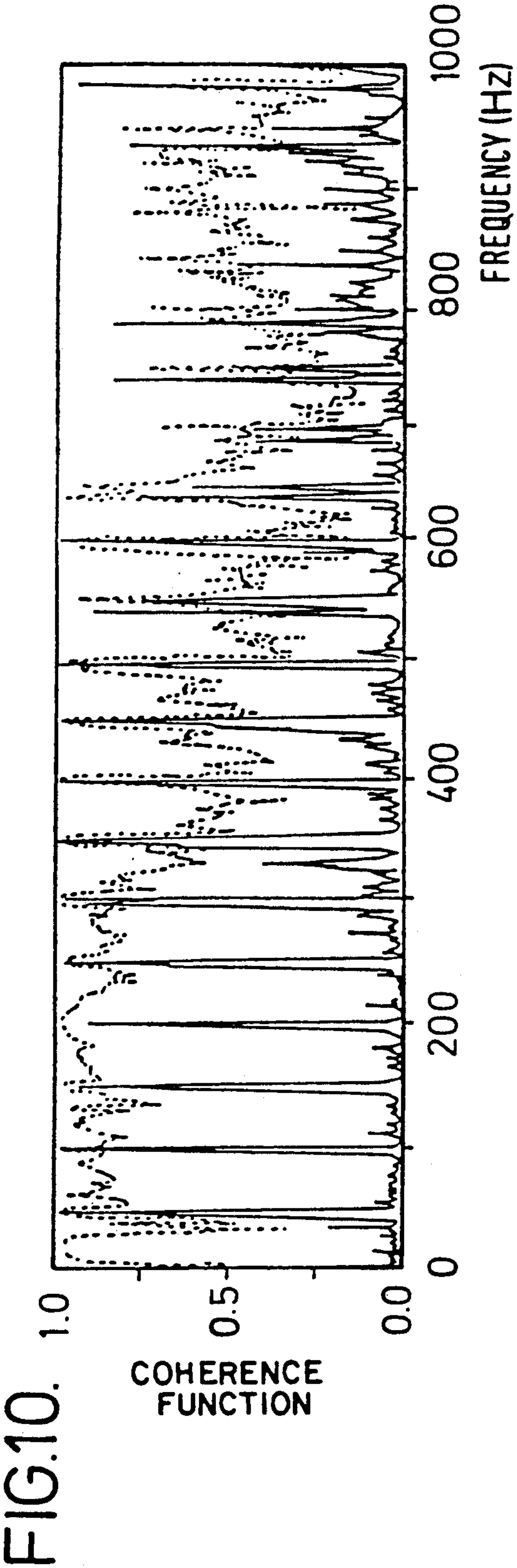
FIG. 10 is a graph showing the coherence function between compressor vibration in the X direction measured at the vibration pick-up mounting position of the FIG. 9 and the compressor noise.
Figure 11:
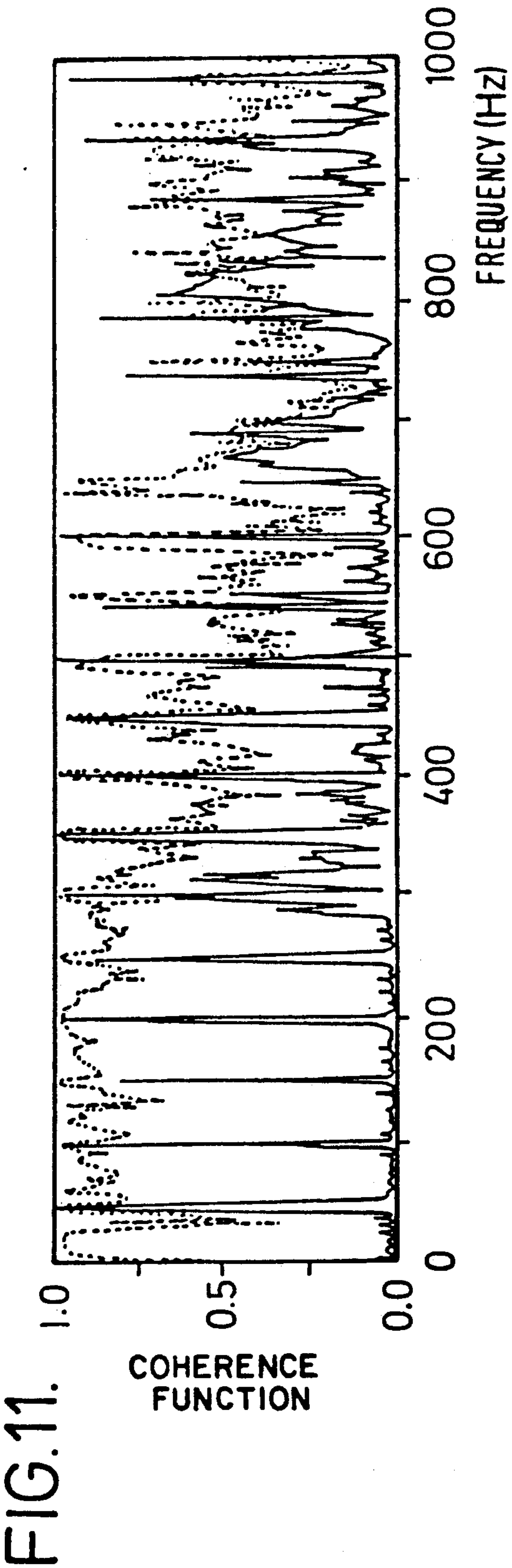
FIG. 11 is a graph showing the coherence function between compressor vibration in the Y direction measured on the circumferential surface of the motor of the compressor and the compressor noise.

FIG. 10 shows the coherence function between the vibration in the X direction measured at the vibration pick-up mounting position of FIG. 9. FIG. 11 shows the coherence function between vibration in the Y direction measured on the circumferential surface of the motor unit 121 of the compressor 120 and the compressor noise. These coherence functions are shown in FIGS. 10 and 11 by the continuous lines and the compressor noises are detected by the evaluation microphone. The broken lines in the FIGS. 10 and 11 indicate the coherence functions between the noise which is detected by the noise source detecting microphone and the noise which is detected by the evaluation microphone. As shown in FIGS. 10 and 11, there is good correlation between the vibration and noise of the compressor 120. That is, in this case also, measurement of the compressor vibration can be adopted instead of detecting compressor noise S.

In these embodiments, real-time control is performed by using an FIR filter 143 in the control circuit 140. It would be possible to perform control with for example a delay of one cycle. As a countermeasure to drift of the silencing transfer function G caused by change with time or solid state differences, so-called adaptive control, in which the transfer function G is automatically suitably altered, can be adopted.

Numerous other modifications and variations of the present invention are possible in light of the above teachings. It is therefore to be understood that, within the scope of the appended claims, the present invention can be practiced in a manner other than as specifically described herein.

What is claimed is:

1. A refrigerator having a silencer system comprising:

a rotary compressor for compressing a refrigerant, the rotary compressor constituting a substantial noise source;

a machine chamber for accommodating said rotary compressor, wherein the machine chamber is provided with an opening in one location, the machine chamber having a one-dimensional duct construction in which a cross-sectional dimension of the duct is sufficiently small relative to the wavelength of said compressor noise to be reduced;

a vibration pick-up for detecting compressor vibrations in the tangential direction of said rotary compressor, wherein the compressor vibrations are representative of said compressor noise, the vibration pick-up being located in the vicinity of said rotary compressor;

a control circuit for processing an output signal of said vibration pick-up; and a sound generator for generating a control sound corresponding to said compressor noise, wherein the sound generator is driven by an output signal from said control circuit.

2. A refrigerator as recited in claim 1, further comprising means for mounting said vibration pick-up, the mounting means being a projection on a circumferential surface of said rotary compressor.

3. A refrigerator as recited in claim 2, wherein said mounting means is a plate-shaped jig.

4. A refrigerator as recited in claim wherein said control circuit is equipped with a finite impulse response filter for processing a signal directly in the time domain.

5. A refrigerator as recited in claim 1, wherein said control circuit has a transfer function G, whereby the transfer function G is determined by the following equations:

$$G = -G_{MR}/G_{AR}$$

$$G_{MR} = G_{SR}/G_{SM}$$

where $G_{AR}$ is a sound transfer function between said sound generator and said opening, $G_{SR}$ is a sound transfer function between said rotary compressor and said opening, $G_{SM}$ is a sound transfer function between said rotary compressor and said vibration pick-up.

6. A refrigerator as recited in claim 1, wherein said rotary compressor is arranged substantially at the farthest position from said opening within said machine chamber.

7. A refrigerator as recited in claim 1, wherein said sound generator is provided in said machine chamber close to said opening.

8. A refrigerator as recited in claim 6, wherein said sound generator is provided in said machine chamber close to said opening.

9. A refrigerator as recited in claim 1, wherein said sound generator is a speaker.

10. A refrigerator having a silence system comprising:

a rotary compressor including a motor unit for compressing a refrigerant, the rotary compressor constituting a substantial noise source;

a machine chamber for accommodating said rotary compressor, wherein the machine chamber is provided with an opening in one location, the chamber having a one-dimensional duct construction in which a cross-sectional dimension of the duct is small relative to the wavelength of said compressor noise to be reduced;

a vibration pick-up for detecting compressor vibrations in the tangential direction of said rotary compressor, wherein the compressor vibrations are representative of said compressor noise, the vibration pick-up being located in close vicinity to said motor unit of said rotary compressor;

a control circuit for processing an output signal of said vibration pick-up; and a sound generator for generating a control sound corresponding to said compressor noise, wherein the sound generator is driven by an output signal from said control circuit.

11. A refrigerator as recited in claim 10, wherein said vibration pick-up is mounted on an end face of said motor unit.

12. A refrigerator as recited in claim 10, further comprising means for mounting said vibration pick-up, the mounting means being a projection on an end face of said motor unit.

13. A refrigerator as recited in claim 12, said mounting means is a bolt.

14. A method for noise controlling a refrigerator eqiupped with a vibration pick-up located in the vicinity of a rotary compressor and a sound generator provided in a machine chamber of the refrigerator, the machine chamber having a one-dimensional duct construction in which a cross-sectional dimension of the duct is sufficiently small relative to the wavelength of said compressor noise to be reduced, the method comprising the steps of:

detecting a tangential component of said rotary compressor vibrations with said vibration pick-up, said vibrations representing the noise generated from said rotary compressor;

processing an output signal of sid vibration pick-up to determine amplitude and frequency of a control sound to be generated in response to said rotary compressor noise; and driving said sound generator to generate siad control sound for canceling said rotary compressor noise by interference action.

* * * * *